United States Patent [19]

Hofmann et al.

[11] Patent Number: 5,658,287
[45] Date of Patent: Aug. 19, 1997

[54] LOCKED INTRAMEDULLARY NAIL, SUITABLE IN PARTICULAR FOR FRACTURES OF THE FEMUR

[75] Inventors: Roberto Hofmann, Lissone; Mario Caniggia, Poggibonsi; Pietro Maniscalco, Parma, all of Italy

[73] Assignee: Gruppo Industriale Bioimpianti S.R.L., Milan, Italy

[21] Appl. No.: 657,184

[22] Filed: Jun. 3, 1996

[30] Foreign Application Priority Data

Jun. 5, 1995 [IT] Italy .................. MI95A1160

[51] Int. Cl.$^6$ .................................... A61B 17/72
[52] U.S. Cl. ............................... 606/63; 606/64
[58] Field of Search ....................... 606/62, 63, 64, 606/67, 68, 65, 66, 60, 105

[56] References Cited

U.S. PATENT DOCUMENTS

| | | | |
|---|---|---|---|
| 5,112,333 | 5/1992 | Fixel | 606/62 |
| 5,263,955 | 11/1993 | Baumgart et al. | 606/63 |
| 5,505,734 | 4/1996 | Caniggia et al. | 606/63 |

Primary Examiner—Michael Buiz
Assistant Examiner—David O. Reip
Attorney, Agent, or Firm—Cushman Darby & Cushman IP Group of Pillsbury Madison & Sutro LLP

[57] ABSTRACT

A locked intramedullary nail suitable for treating fractures of the femur, including a pin provided with proximal and distal holes for the passage of locking screws, and further including coaxial tubular elements of greater diameter than the pin, the first of which is mounted from the proximal end on the pin and is provided with restraining means which prevent its rotation about the pin but which enable it to translate along its axis as far as a stop, the first element comprising an upper thread and holes for the passage of the proximal locking screws, between the thread and said holes it being to a certain extent elastically yieldable in the manner of a spring by the effect of spiral slits provided through its lateral surface, the second of the coaxial tubular elements being mounted on said first element and engaging it via a thread of opposite hand to that of the first element, while at the same time engaging the proximal end of the pin by screwing, so that while said second element screws onto the pin it unscrews at the same time from the first element, which hence translates along the pin to withdraw from its proximal end.

3 Claims, 3 Drawing Sheets

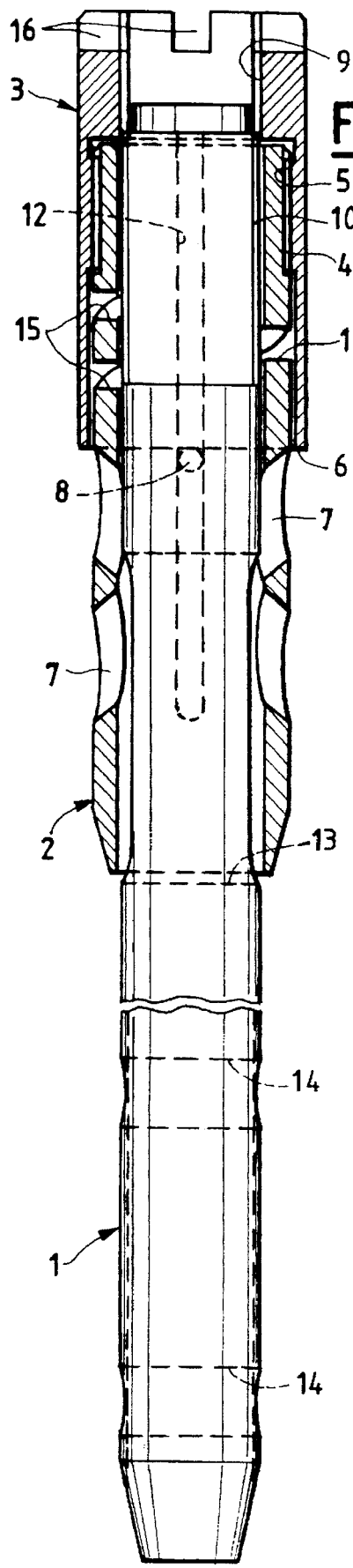
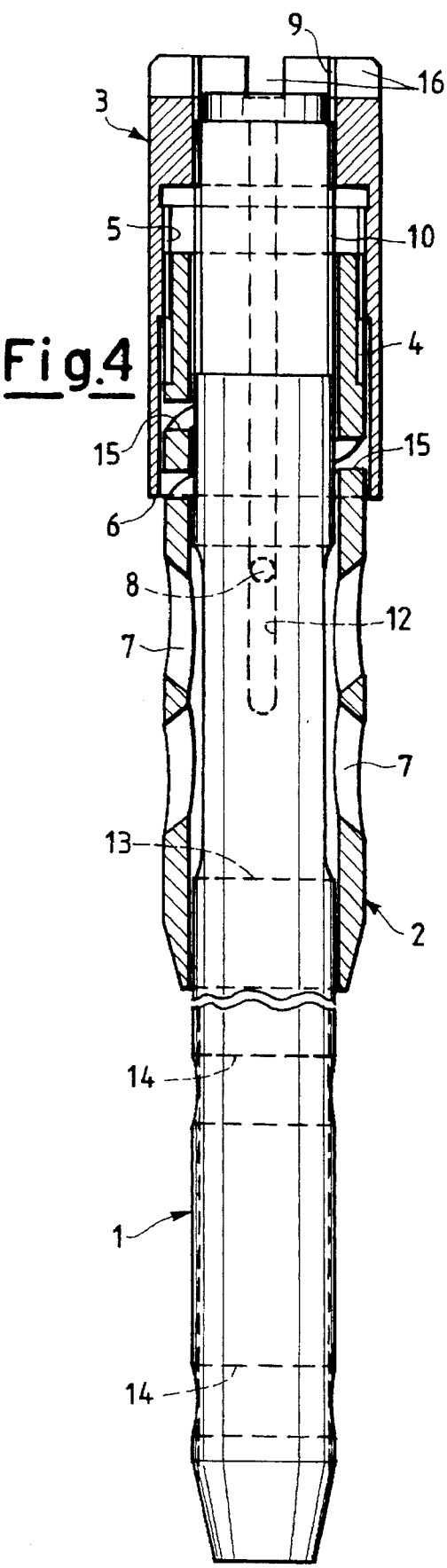

LOCKED INTRAMEDULLARY NAIL, SUITABLE IN PARTICULAR FOR FRACTURES OF THE FEMUR

In recent years, intramedullary nailing has become one of the most widespread and efficient synthesis systems, often in opposition to external circular and monolateral fixing and to open-roofed osteosynthesis methods (plates and screws). For an example of an intramedullary nail suitable for fractures of the humerus, reference should be made to U.S. patent application Ser. No. 08/318,158 of the present Applicants.

The reasons for this propagation of intramedullary nailing lie in the greater tolerability by the patient and the reduced surgical impact.

The present invention relates to this type of technique relative to intramedullary nails, in particular with regard to treating fractures of the lower limbs, and specifically fractures of the femur.

Currently available femoral nails have certain drawbacks which can be summarized as follows:

- the problem of considerable rigidity of the synthesis means which substantially diverts the physiologic load from the fractured segment, to reduce the rate of callus formation, which has been shown to be most rapid in the presence of a small physiologic load (absence of pumping effect);
- the difficulty of compressing the fracture rima during the implant, and in particular the impossibility of maintaining dynamic compression during the postoperative period;
- the possibility of localized mechanical stresses on the proximal and distal locking screws of the femoral nail, with consequent mobilization of the synthesis means and possible consequent osteolytic phenomena.

For these reasons, an object of the present invention is to provide a femur nailing means which enables the fracture rima to be dynamically compressed while at the same time incorporating a device able to absorb sudden impacts causing stressing of the bone anchoring screws.

It has also been sought to implement a device which ensures considerable stability while at the same time providing the nail-bone system with elasticity to produce that effect of dynamic compression during the post-operative period which according to the most recent and accredited theories most favours the healing of the fracture.

These objects and further advantages while will be apparent from the ensuing description are attained according to the present invention by a locked intramedullary nail suitable in particular for treating fractures of the femur, of the type comprising a pin provided with proximal and distal holes for the passage of locking screws, characterised by comprising a pair of coaxial tubular elements of greater diameter than the pin, the first of which is mounted from the proximal end on said pin and is provided with restraining means which prevent its rotation about the pin but which enable it to translate along its axis as far as a stop, said first element comprising an upper thread and holes for the passage of said proximal locking screws, between said thread and said holes it being to a certain extent elastically yieldable in the manner of a spring by the effect of spiral slits provided through its lateral surface, the second of said coaxial tubular elements being mounted on said first element and engaging it via a thread of opposite hand to that of said first element, while at the same time engaging the proximal end of said pin by screwing, so that while said second element screws onto said pin it unscrews at the same time from said first element, which hence translates along the pin to withdraw from its proximal end.

The characteristics and advantages of the invention will be more apparent from the description of one embodiment thereof given hereinafter with reference to the accompanying drawings. This embodiment is not to be considered as limitative but merely illustrative of the invention.

With reference to said drawings:

FIGS. 3 and 4 are partly sectional views showing the nail complete with its elements in two different operating positions.

Figure 1:
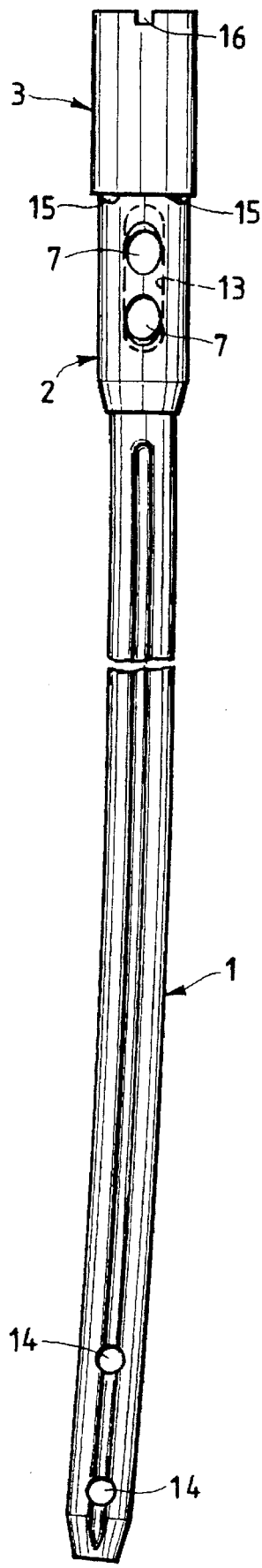
FIG. 1 is an elevation of an intramedullary nail according to the invention complete with its constituent elements, assembled in their operating position.

With reference to these figures, an intramedullary nail of the invention, particularly suitable for fractures of the femur, is composed of a pin 1 threaded upperly with a thread 10 and comprising in its proximal region a pair of holes in the form of facing slots 13, and in its distal end two pairs of facing holes 14.

The slots 13 and holes 14 serve for the passage of screws for locking the intramedullary nail to the fractured bone. The pin 1 is also provided in its proximal region with a longitudinal groove 12 which passes entirely through the thread 10 and extends between the slots 13 as far as about one half of their length.

Figure 2:
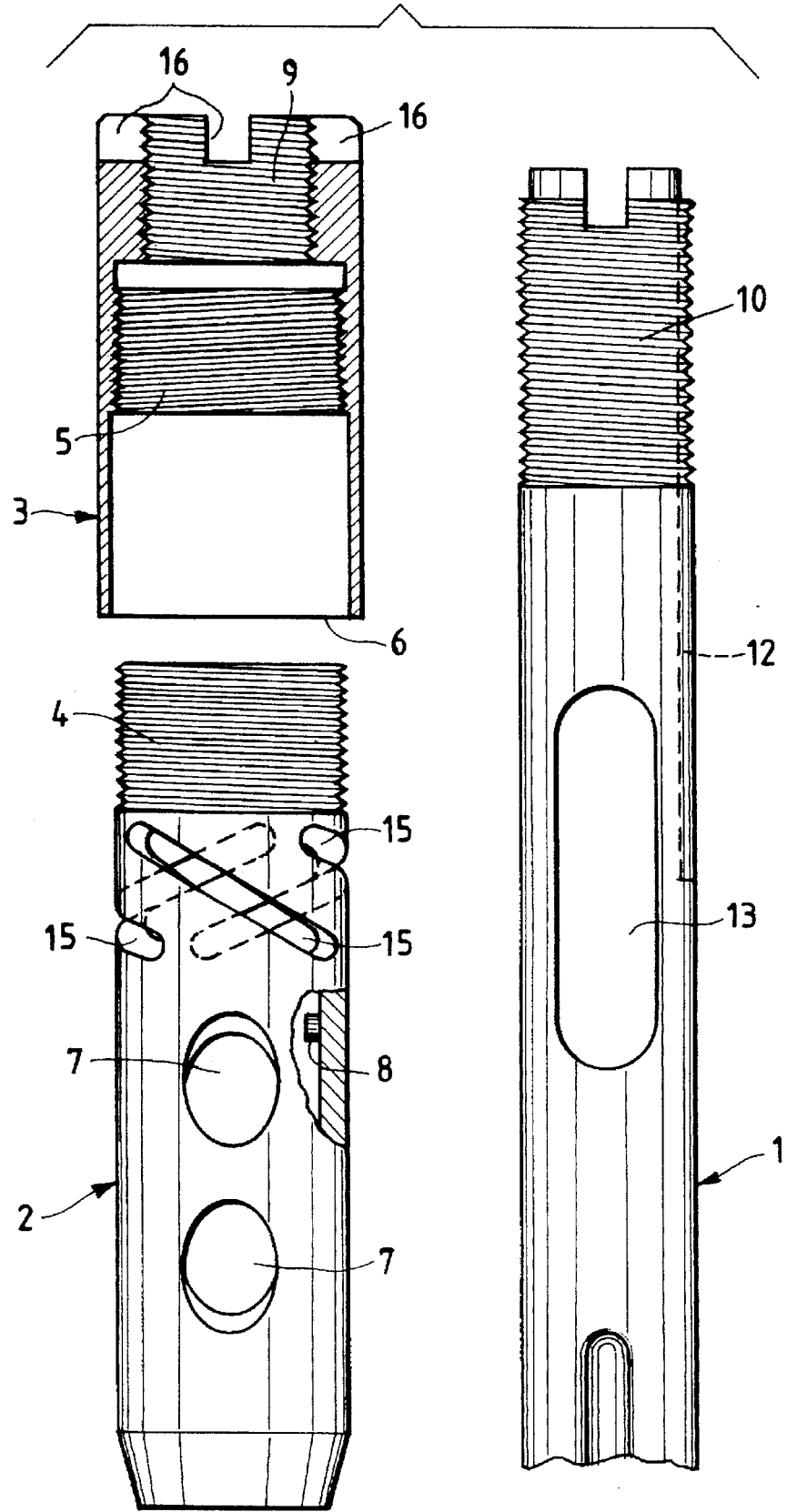
FIG. 2 is a partly sectional exploded elevation showing the components of the nail of FIG. 4.

As shown in FIG. 2, with the pin 1 there cooperate in the proximal region a pair of coaxial tubular elements consisting of a first element 2 with a lateral hole for the passage of the proximal nail locking screws, the element 2 being threaded upperly at 4 and being provided with a tooth 8 to be inserted into the groove 12 in the pin 1 so as to prevent it rotating about the pin, it being however able to translate along the pin axis. The element 2 comprises two pairs of flared holes 7 allowing transverse passage of the fixing screws.

When in the operating position the pairs of holes 7 hence face the pair of slots 13 in the pin.

Said element 2 is lowerly tapered, and is of greater diameter than the pin so that it can slide on it in correspondence with the tooth 8 which translates within the groove 12 until the tooth 8 abuts against the end of said groove, which hence forms a stop for the element 2 translating coaxially on the pin 1.

There is a further coaxial tubular element 3 of greater diameter than the element 2 and carrying a double thread, namely a first thread 9 of the same hand as the thread 10 of the pin and with which it engages, and a second thread 5 to engage the thread 4 of the element 2, and being of opposite hand to this latter.

The element 3 terminates upperly with slots 16, for example of four in number equidistant along the upper end of 3, to receive a suitable screwdriver to be used by the surgeon for screwing and unscrewing the piece 3.

In the region between the thread 4 and the first pair of holes 7, the tubular element 2 comprises, through its surface, parallel slits provided in an inclined direction in the manner of the turns of a spring. These slits 15 function in fact as the turns of a spring, so that the effect of the slits is to provide the element 2 with a certain elastic yieldability under the action of a suitable load.

For this reason the element 2 will be known hereinafter as the spring body.

The intramedullary nail shown in the figures operates as follows. To implant the nail, the element 3 is screwed right down on the spring body 2. As the thread 4 on the spring body 2 is of opposite hand to the thread of the element 3, the direction in which 3 is screwed down on 2 is anticlockwise.

When completely screwed down, the lower edge 6 of the element 3 is flush with the pair of holes 7 in the spring body.

When in this position, the assembly formed from the elements 3 and 2 is fixed onto the pin 1.

For this, the assembly 2–3 is mounted on the pin 1 so that the tooth 8 engages in the groove 12 in the pin, and is slid down until its end of travel.

The engagement between the groove 12 and tooth 8 means that the spring body 2 is unable to rotate on the pin 1.

The element 3 can however rotate about the pin 1 to allow screwing via the threads 9 and 10, which are of equal hand and hence tightenable clockwise by the action of a special screwdriver engaging the appropriate slots 16.

Hence on screwing down the element 3, rigid with the element 2, on the proximal end of the pin 1, the rotary screwing movement of the element 3 produces simultaneous unscrewing between the thread 5 of the element 3 and the thread 4 of the spring body 2, so that they withdraw from each other.

Essentially, the rotary screwing movement of the element 3 is transmitted to the spring body rigid with it in the form of a translational movement along the pin 1, as the spring body is unable to rotate about the pin.

Hence screwing the element 3 on the pin 1 by rotating 3 clockwise produces two effects, namely the screwing down of the element 3 on the pin 1 and the unscrewing of the element 3 from the spring body 2. This means that the pairs of holes 7 provided in the spring body 2 move relative to the slot 13 in the pin, towards which said pairs of proximal holes face.

On this basis, having made the preparations necessary for implanting the nail, the surgeon arranges it in the position shown in FIG. 3. Then after positioning the intramedullary nail in its seat within the bone so that it passes suitably through this latter in correspondence with the fracture rima, he then applies the locking screws distally and proximally through the pairs of holes 14 and 7 respectively.

At this point, having positioned the locking screws, he then proceeds from the initial position of the nail shown in FIG. 3 to the operating position shown in FIG. 4, in which the spring body progressively compresses, to the desired extent, the locking screws positioned transversely in the proximal region within the nail and bone under the regulating action of the element 3. By screwing down the element 3, this compression of the spring body on the locking screws can be suitably adjusted to the desired degree.

This system essentially enables the seat of the fracture to be compressed to a maximum length corresponding to 10 mm while maintaining identical dynamic response characteristics of the spring formed by the element 2 in any position in which it lies along the nail axis.

In other words, by the effect of the spring body structured in this manner, the patient can load his own weight onto the fractured bone with the impact consequent on this load being absorbed as in the case of a shock absorber, while the fracture rima is stressed by the load so as to facilitate osseous callus formation.

At the same time, this shock absorber system prevents localized mechanical stresses arising on the proximal and distal locking screws, hence avoiding the risk of instability of the synthesis means.

It will be noted that the initially stated objects are effectively attained by the invention.

According to a modification of the invention, the same intramedullary nail can be used not to compress the locking screws, but to achieve a strain effect at the fracture rima when the treatment requires it.

For this purpose, instead of screwing the compression regulating element clockwise, it is merely screwed anticlockwise to achieve the required adjustment.

According to the invention, the desired elastic absorption effect is essentially achieved by a spring formed integrally in the element 2, i.e. without the need to interpose any additional spring which would be of unacceptable dimensions and bulk considering the loads in question at the femoral level.

Instead, in the case of the invention, there is the considerable advantage of reduced length and diameter of the compression device, which do not exceed the allowable dimensions in the proximal part of the femur.

Essentially, the synthesis means of the invention is no more invasive than known femoral nails, while at the same time presenting the aforedescribed characteristics which are completely innovative, as femoral nails able to act at the same time as a shock absorber for impacts and loads suffered by the bone do not exist.

We claim:

1. A locked intramedullary nail suitable for treating fractures of the femur, comprising a pin provided with proximal and distal holes for the passage of locking screws; and first and second coaxial tubular elements of greater diameter than the pin, the first of which is mounted from the proximal end on said pin and is provided with restraining means which prevent its rotation about the pin but which enable it to translate along its axis as far as a stop, said first element comprising an upper thread and holes for the passage of said proximal locking screws, between said thread and said holes it being to a certain extent elastically yieldable in the manner of a spring by the effect of spiral slits provided through its lateral surface, the second of said coaxial tubular elements being mounted on said first element and engaging it via a thread of opposite hand to that of said first element, while at the same time engaging the proximal end of said pin by screwing, so that while said second element screws onto said pin it unscrews at the same time from said first element, which hence translates along the pin to withdraw from its proximal end.

2. A nail as claimed in claim 1, wherein said slits are provided parallel to each other in an inclined direction along said lateral surface of said first element.

3. A nail as claimed in claim 1, wherein said restraining means comprises a protrusion provided on the inner surface of said first element, to engage a longitudinal groove provided in the outer surface of said pin in the proximal region.

* * * * *